United States Patent

Jones et al.

(10) Patent No.: US 6,254,588 B1
(45) Date of Patent: *Jul. 3, 2001

(54) MICROCATHETER

(75) Inventors: Michael L. Jones, Capistrano Beach; Scott Evans, Santa Ana; George B. Wallace, Coto de Caza, all of CA (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/075,792

(22) Filed: May 12, 1998

Related U.S. Application Data

(63) Continuation of application No. 08/556,626, filed on Nov. 13, 1995, now Pat. No. 5,843,050.

(51) Int. Cl.[7] .................................................. A61M 25/00
(52) U.S. Cl. .......................................... 604/525; 604/527
(58) Field of Search .................................. 604/523, 525, 604/526, 527

(56) References Cited

U.S. PATENT DOCUMENTS

| | | | |
|---|---|---|---|
| 4,495,134 | 1/1985 | Ouchi et al. | 264/516 |
| 4,516,972 | * 5/1985 | Samson | 604/525 |
| 4,669,172 | 6/1987 | Petruzzi | 264/516 |
| 4,739,768 | 4/1988 | Engelson | 264/516 |
| 4,941,877 | 7/1990 | Montano, Jr. | 264/516 |
| 4,955,862 | 9/1990 | Sepetka | 264/516 |
| 4,960,410 | 10/1990 | Pinchuk | 604/523 |
| 5,085,635 | 2/1992 | Cragg | 604/523 |
| 5,178,158 | 1/1993 | de Toledo | 604/523 |
| 5,358,493 | 10/1994 | Schweich, Jr. et al. | 604/523 |
| 5,380,304 | 1/1995 | Parker | 604/526 |
| 5,405,304 | 4/1995 | Kranys | 604/526 |
| 5,437,288 | 8/1995 | Schwartz et al. | 604/526 |
| 5,454,795 | 10/1995 | Samson | 604/526 |
| 5,545,132 | 8/1996 | Fagan et al. | 604/526 |
| 5,573,520 | 11/1996 | Schwartz et al. | 604/526 |
| 5,676,659 | * 10/1997 | McGurk | 604/525 X |
| 5,843,050 | * 12/1998 | Jones et al. | 604/525 |
| 5,851,203 | * 12/1998 | Van Muiden | 604/525 |

FOREIGN PATENT DOCUMENTS

| | | |
|---|---|---|
| 0 029 185 | 5/1981 | (EP) . |
| 0 631 791 | 1/1995 | (EP) . |
| 0 643 979 | 3/1995 | (EP) . |
| 0 718 003 | 6/1996 | (EP) . |
| WO95/13110 | 5/1995 | (WO) . |

* cited by examiner

*Primary Examiner*—Anh-Tum T. Nguyen
(74) *Attorney, Agent, or Firm*—Burns Doane Swecker & Mathis, LLP

(57) ABSTRACT

Disclosed is an elongate flexible microcatheter, for diagnostic and or therapeutic applications. The microcatheter is provided with a small outside diameter and high degree of flexibility, to facilitate negotiation of small, tortuous vessels such as those encountered in intercranial catheterizations. The catheter is formed from a composite of a series of tubular elements, each extending axially for a different distance along the tubular body. A distal section on one or more of the tubular components is provided with a spiral cut, to modify the flexibility properties of the finished catheter. The catheter may also be provided with an inflatable balloon, and a valve to permit the use of a single lumen for both receiving a guidewire and for conveying inflation media.

13 Claims, 4 Drawing Sheets

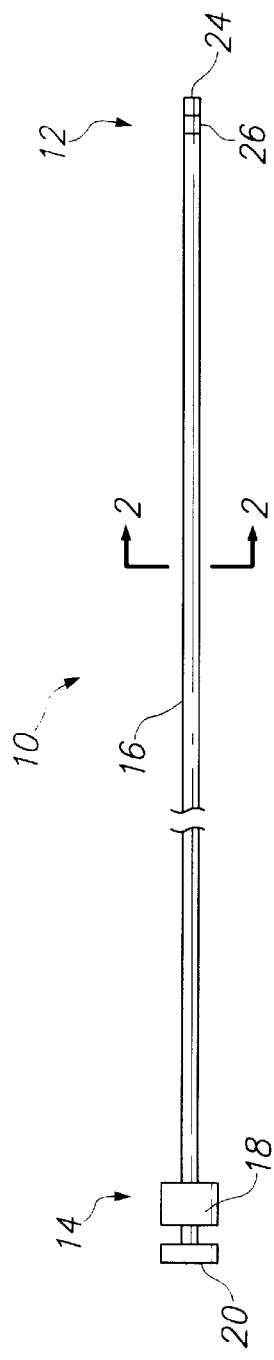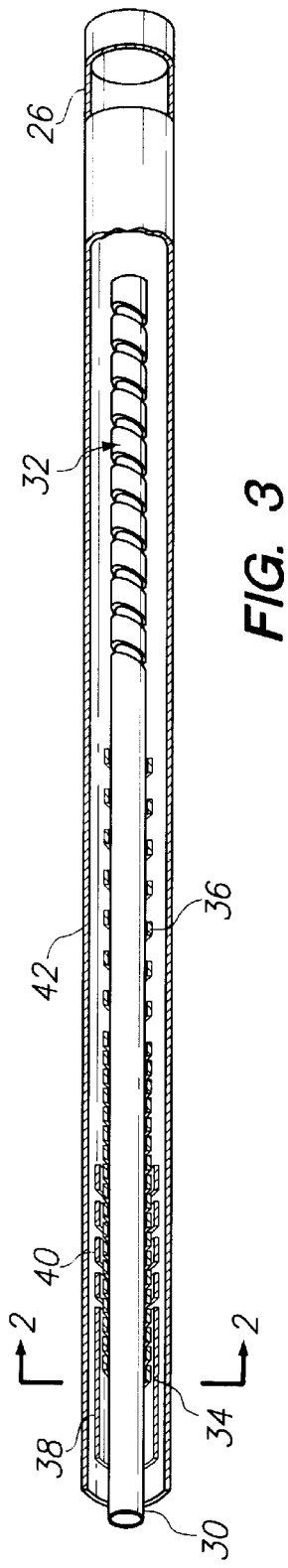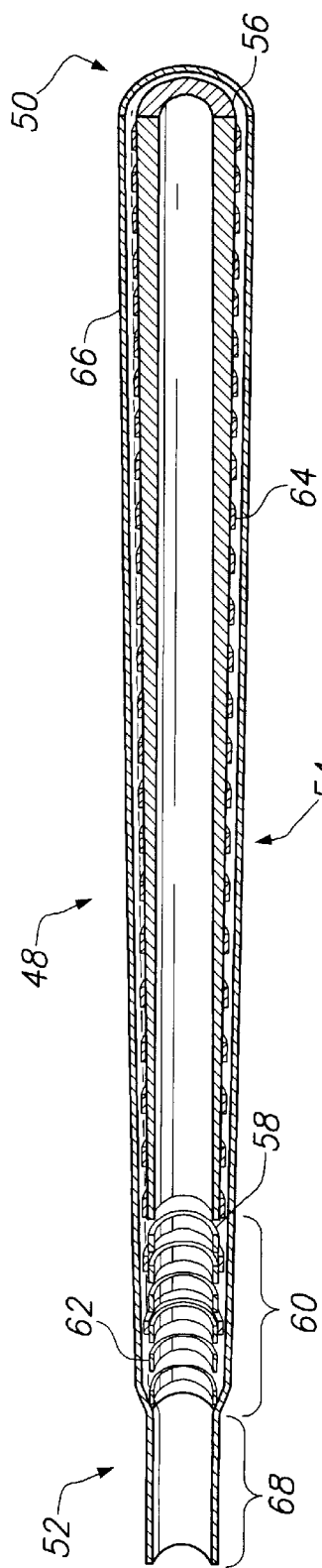

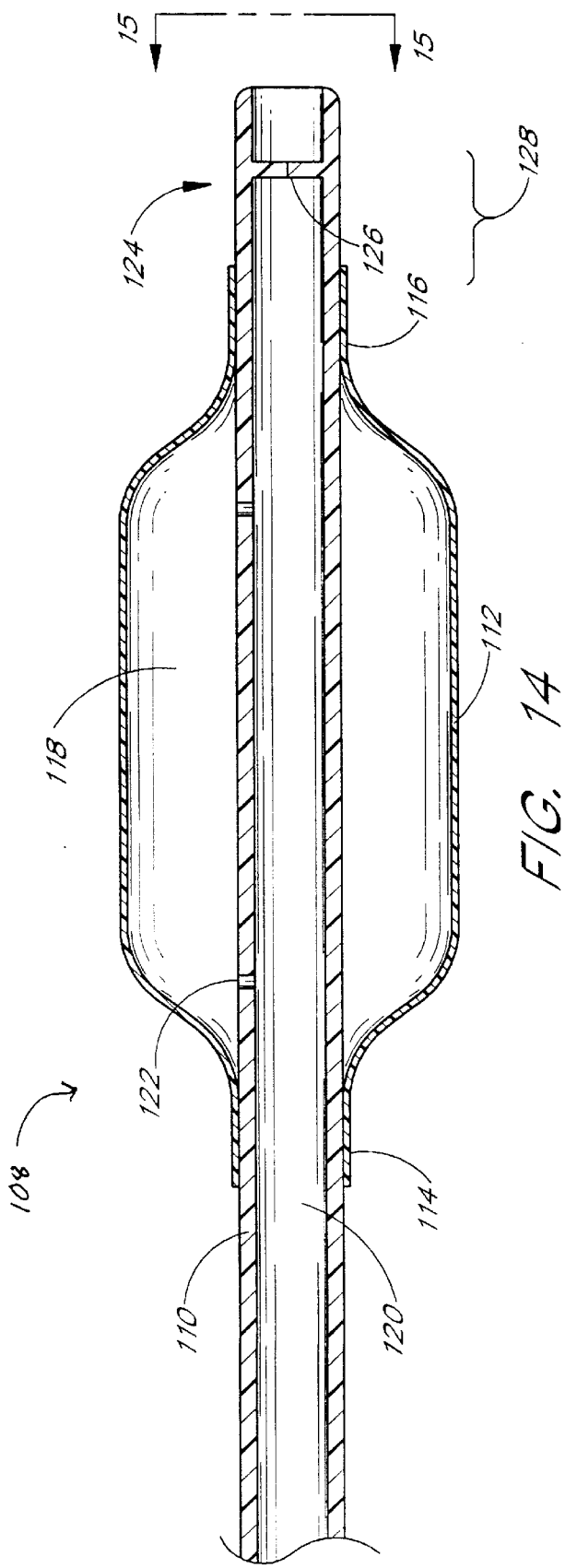
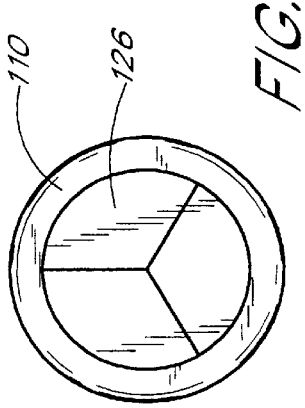
FIG. 14
FIG. 15

MICROCATHETER

This application is a continuation, of application Ser. No. 08/556,626, filed Nov. 13, 1995 now U.S. Pat. No. 5,843,050.

BACKGROUND OF THE INVENTION

The present invention relates to catheters for medical diagnostic or therapeutic use. In particular, the present invention relates to microcatheters of the type particularly adapted for navigating tortuous pathways in soft tissues, such as the brain.

A wide variety of catheters have been developed, for percutaneous insertion into the vascular system to accomplish any of a number of diagnostic or therapeutic objectives. For example, a wide variety of balloon dilatation catheters adapted for percutaneous transluminal coronary angioplasty are known. Peripheral vascular dilatation catheters, angiography catheters, drug delivery catheters and others are well represented in the prior art.

However, due to the relatively large diameter and minimal tortuosity of the peripheral vasculature and, to a lesser extent, the coronary vasculature, the prior art catheters are typically unsuited for use in the small tortuous vessels, such as those found in the soft tissue of the brain and liver. In addition to size constraints imposed by such soft tissue vasculature, catheters suitable for these applications must also exhibit optimal flexibility, while at the same time maintaining adequate column strength and other desirable properties. In general, the known catheters for one reason or another are unsuited for intercranial catheterizations. Such catheterizations are useful for a variety of diagnostic and interventional neurological techniques including drug delivery, imaging, treatment of aneurysms, tumors, arterio-venous malformations, and the like.

For example, in angiography, catheters are designed to deliver a radio-opaque agent to a target site within a blood vessel, to allow radiographic viewing of the vessel and blood flow characteristics near the release site. For the treatment of localized disease, such as solid tumors, catheters allow a therapeutic agent to be delivered to the target site at a relatively high concentration, with minimum overall side effects. Methods for producing localized vaso-occlusion in target tissue regions, by catheter injection of a vaso-occlusive agent, have also been described.

Often the target site which one wishes to access by catheter is buried within a soft tissue, such as brain or liver, and is only reached by a tortuous route through vessels or ducts typically having less than about a 3 mm lumen diameter. The difficulty in accessing such regions is that the catheter must be quite flexible, in order to follow the tortuous path into the tissue and, at the same time, stiff enough to allow the distal end of the catheter to be manipulated from an external access site, which may be as much as a meter or more from the target site.

Two general methods for accessing such tortuous-path regions have been devised. The first method employs a highly flexible catheter having a inflatable, but pre-punctured balloon at its distal end. In use, the balloon is partially inflated, and carried by blood flow into the target site. The balloon is continually inflated during placement to replenish fluid leaking from the balloon. A major limitation of this method is that the catheter will travel in the path of highest blood flow rate, so many target sites with low blood flow rates cannot be accessed.

In the second prior art method, a torqueable guide wire having a distal bend is guided, by alternatively rotating and advancing the wire, to the target site. With the wire in place, the catheter is then advanced along the wire until the distal catheter is then advanced along the wire until the distal catheter end is positioned at the target site. An important advantage of this method is the ability to control the location of the catheter along a tortuous path. Torqueable guide wires which can be guided into delicate, tortuous, and narrow vasculature are available. However, it is often difficult or impossible to advance a catheter over the wire, especially where the wire extends along a tortuous path of more than about 10 cm. If the catheter is relatively rigid, it cannot track over the final distal portion of the wire in the tortuous path region, because catheter advancement buckles the wire in a narrow turn, or because catheter advancement pulls the wire out of the distal vessels. On the other hand, catheters having more flexible shafts, such as those used in balloon flow-directed devices, lack the column strength in the catheter's proximal section to be advanced over the guide wire without buckling.

The need in the art for suitably flexible and small diameter medical catheters is exemplified by the statistical prevalence of vascular disorders of the brain associated with stroke. Stroke is currently the third leading cause of death in the United States with an estimated annual cost of $30 billion. In the United States alone, stroke affects in excess of 500,000 Americans annually, resulting in 150,000 deaths. Current treatment options are relatively limited and generally highly invasive.

Thus, there remains a need in the art for the development of catheters useful in minimally invasive procedures to diagnose and treat vascular diseases of the brain, such as those associated with stroke, and other diseased sites accessible through only the small vessels of the circulatory system.

SUMMARY OF THE INVENTION

In accordance with one aspect of the present invention, there is provided a microcatheter for negotiating small tortuous vessels. The catheter comprises an elongate flexible body, having a tubular wall and at least one lumen extending axially therethrough. A first tubular element is provided in the wall, extending from a proximal end of the catheter through the body and terminating in a first distal zone. A second tubular element is provided in the wall, extending axially from a proximal end of the catheter through the tubular body and terminating in a second distal zone. Each of the first and second tubular elements is provided with a spiral cut in each of the first and second distal zones.

Preferably, the first tubular element is disposed coaxially within the second tubular element. The second distal zone is preferable axially displaced from the first distal zone.

In one embodiment, the catheter further comprises a spring coaxially disposed within the tubular wall. The spring may be positioned on the radially exterior side of the first tubular element and on the radially interior side of the second tubular element.

In accordance with another aspect of the present invention, there is provided a method of manufacturing a highly flexible small diameter catheter. The method comprises the steps of providing an elongate tubular element having a distal zone in which the tubular element is provided with a first spiral cut.

A spring coil is positioned coaxially about the outside of the first tubular element, such that the spring coil extends distally from a proximal end of the catheter to a point which is spaced apart proximally from the distal end of the first tubular element.

Preferably, a second tubular element is provided having a proximal solid walled zone and a distal spiral cut zone. The second tubular element is positioned coaxially about the spring coil, such that the second tubular element extends from the proximal end of the catheter to a point which is proximal to the distal end of the spring coil.

Preferably, an outer tubular jacket is positioned around the outside of the subassembly formed above, and the outer tubular jacket is radially reduced such as by the application of heat to form a highly flexible small diameter catheter.

Further features and advantages will become apparent from the detailed description of preferred embodiments which follows, when considered together with the attached drawings and claims.

BRIEF DESCRIPTION OF THE DRAWINGS

FIG. 1 is a side elevational view of a microcatheter in accordance with one aspect of the present invention.

FIG. 3 is a fragmentary cross-sectional side elevational representation of the catheter of FIG. 1.

FIG. 4 is a side elevational cross-sectional view of an alternate embodiment of a microcatheter in accordance with the present invention.

FIG. 14 is a side elevational view of the distal end of a balloon microcatheter in accordance with the present invention.

FIG. 15 is an end elevational view taken along the lines 15—15 in FIG. 14.

DETAILED DESCRIPTION OF THE PREFERRED EMBODIMENT

Figure 2:
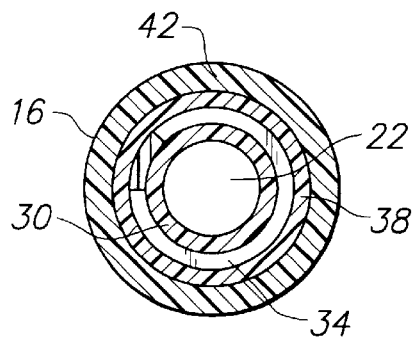
FIG. 2 is a cross-sectional view along the lines 2—2 of FIG. 1.

Referring to FIG. 1, there is disclosed a microcatheter 10 in accordance with one aspect of the present invention. Microcatheter 10 generally comprises a distal end 12, a proximal end 14, and an elongate flexible tubular body 16 extending there between.

In an embodiment adapted for intercranial catheterizations, the catheter body 16 will generally have an outside diameter within the range of from about 0.5 mm to about 1.5 mm. The length of the microcatheter 10 will generally be in the range of from about 150 cm to about 175 cm. Other dimensions than those disclosed above and recited elsewhere herein can be readily utilized by those of ordinary skill in the art in view of the disclosure herein to suit particular intended uses of the microcatheter 10.

The proximal end 14 of microcatheter 10 is preferably provided with a manifold 18. Manifold 18 is provided with at least one access port 20, such as for communicating with distal access port 24 by way of an elongate central lumen 22 (see FIG. 3). Central lumen 22 permits the microcatheter 10 to track over a guide wire as is well understood by those of skill in the art. In addition, following placement of the microcatheter 10, as will be discussed in greater detail below, the guide wire can be removed and central lumen 22 used to infuse medication or permit the accomplishment of other diagnostic or therapeutic procedures.

In general, the inner diameter of the central lumen 22 is dimensioned with respect to the outside diameter of the guidewire to provide sufficient wire clearance to allow the catheter to be moved easily over the wire in an axial direction, during catheter placement at the target site. The guidewire preferably has a relatively small diameter, to permit its guided movement along a tortuous path in a target tissue. A preferred guidewire designed for accessing a target along a tortuous path has a diameter within the range of from about 0.008 inches to about 0.018 inches. The guidewire is preferably formed of a material such as stainless steel which is torqueable, yet flexible in fiber or filament form. Smaller diameter guidewires, such as 0.008 inch wires, are sufficiently flexible to be maneuvered along a tortuous path within a soft tissue. Larger diameter wires, such as 0.014 and 0.018 inch wires, may need to be tapered at their distal end regions to maneuver along such paths. Guidewires having a tapered core distal section with a coil wrapping for greater maneuverability in the distal region of the wire are commercially available. The guidewire has or can be fashioned to have a curved tip, for purposes of guiding the wire along a tortuous vascular path.

The inside diameter of the central lumen 22, particularly in its distal segment, is preferably between about 0.002 to about 0.005 inches larger than the outside diameter of the guidewire for which the catheter is designed. Thus, a catheter designed for use with a 0.018 inch guidewire has a preferred inside diameter of from about 0.020 to about 0.025 inches, and, more preferably, from about 0.021 to about 0.022 inches. The preferred 0.002 to about 0.005 inch total clearance between the wire and inner wall of the catheter reduces the tendency of the catheter to buckle under compressional strain, since the wire provides column support against tubes bending and crimping.

The inside diameter of the central lumen 22 throughout the proximal portions of the catheter may also be from about 0.002 to about 0.005 inches larger in diameter than the outside diameter of the guidewire, thereby providing column support throughout the catheter. However, a larger diameter for central lumen 22 in the proximal segment would permit greater fluid flow through the catheter, in delivering fluid to the target site. In this embodiment, the proximal and distal segments would meet at a step, which would preferably be tapered to provide improved fluid flow and guidewire slidability.

The microcatheter 10 can be provided with a single lumen, as illustrated, or with multiple lumen, depending upon the diameter constraints imposed by the intended use and the functional requirements of the catheter. If desired, the microcatheter can also be constructed with rapid exchange capabilities, such as by providing a guidewire lumen which extends through only a distal section of the microcatheter 10.

Referring to FIG. 3, there is disclosed a nonscale cross-sectional representation of a microcatheter in accordance with one embodiment of the present invention. In this embodiment, the microcatheter 10 is provided with an overall length of about 150 centimeters. The elongate central lumen 22 is defined for at least a proximal portion of the microcatheter 10 within a tubular element 30. Tubular element 30 preferably comprises a polytetrafluoroethylene tube, or other material which optimizes the slidability of the microcatheter 10 over a guide wire (not illustrated).

In the illustrated embodiment, the tubular element 30 extends in a distal direction for at least about 100 centimeters, preferably at least about 140 centimeters, and, in a particular embodiment, for about 148 centimeters. In an embodiment of the present invention in which the microcatheter 10 has an outside diameter in its proximal section of about 0.85 mm, the polytetrafluoroethylene tubular liner 30 has a wall thickness of about 0.002 inches, an inside diameter of about 0.40 mm, and an outside diameter of about 0.51 mm.

A distal section 32 of tubular element 30 is provided with a spiral cut, to modify the physical properties of the catheter as will be described. The spiral cut section 32 generally has a length within the range of from about 1 centimeter to 15 centimeters, preferably within a range of about 5 centimeters to about 12 centimeters, and, in a particular embodiment, extends for approximately 10 centimeters in length. The spiral cut generally has a pitch within the range of from about 0.01 inches to about 0.125 inches, and in one embodiment, has a 0.06 pitch. In another embodiment, the distal section 32 comprises a first spiral cut section having a length of about 5 cm and a pitch of about 0.06, and a second, distal section having a length of about 5 cm and a pitch of about 0.030.

Preferably, the spiral cut extends completely through the wall of the tubular element 30 to produce a helical or coiled configuration. The precise pitch of the spiral cut and axial spacing of adjacent windings can be varied widely while still accomplishing the purposes of the present invention, and can be optimized for any particular application in view of the disclosure herein.

The tubular element 30 in the illustrated embodiment is positioned within a coil spring 34. Preferably, coil spring 34 extends from the proximal end of the catheter in a distal direction for at least about 100 centimeters, although other axial lengths of the coil spring can be readily used depending upon the desired flexibility properties of the catheter.

A distal section 36 of the coil spring 34 is stretched axially to produce an open wound configuration, such that the axial space between adjacent windings of the coil is within the range of from about 0.07 mm to about 1 mm. The proximal portion of coil spring 34 is generally bottomed out, such that adjacent windings of the coil are in contact with one another. Alternatively, the coil spring can be open wound with 0.01 mm to 1 mm spacing for the entire length.

A variety of materials can be used to construct the coil spring 34, such as stainless steel, platinum, platinum alloy, nickel, or titanium alloys. Coil spring 34 can be produced from any of a variety of stock forms, such as round cross-sectional wire, square or other rectangular wire, or polymeric materials as are known in the art. Preferably, coil spring 34 is wound from a flat wire made from stainless steel and having cross-sectional dimensions of about 0.002 by about 0.006 inches.

The coil spring 34 enhances a variety of desirable properties, such as pushability, torqueability, and a resistance to kinking or compression by radially inwardly directed forces. Depending upon the intended use of the catheter, alternate stiffening structures can be employed. For example, one or more axially extending stiffening wires or rods can be provided between the tubular liner 30 and the outer tubular jacket 38 as will be discussed. Optimizing the physical properties of a particular catheter can be readily done by one of ordinary skill in the art in view of the disclosure herein, for any particular intended use of the catheter.

A proximal section of the microcatheter 10 is further provided with a tubular jacket 38 of a relatively stiff material such as polyimide. Alternatively, the jacket 38 may comprise any of a variety of other materials depending upon the desired physical properties of the finished microcatheter 10. For example, jacket 38 may be extruded using polyester or nylon. Alternatively, the jacket 38 may be formed from braided materials or braid containing materials, such as polyimide, polyester, or nylon.

The jacket 38 extends from the proximal end of the catheter in a distal direction for at least about 50 centimeters and preferably within the range of from about 90 to about 125 cm. Preferably, the distal end of the jacket 38 if polyimide is used is positioned along the catheter body such that it will remain positioned within the guiding catheter when in use.

A distal section 40 of tubular jacket 38 is provided with a spiral cut, to modify the flexibility properties of the microcatheter 10. Preferably, at least about the distal most 10 cm of the jacket 38, and, more preferably, about the distal most 5 cm of jacket 38 is provided with the spiral cut. As with the spiral cut on tubular element 30, the spiral cut on the jacket 38 may take any of a variety of forms. However, the present inventor has determined that a spiral cut having about a 0.060 pitch spiral is suitable for the purposes of the present invention.

In the illustrated embodiment, the microcatheter 10 is further provided with an outer tubular jacket 42, made from a heat shrinkable polyolefin such as polyethylene. The outer tubular jacket 42 preferably extends throughout the length of the microcatheter 10, to provide a smooth exterior surface. The distal end 44 of jacket 42 preferably extends beyond the distal end of the polytetrafluoroethylene liner 30. In the illustrated embodiment, the outer jacket 42 preferably extends for about 1 centimeter beyond the distal end of the liner 30.

Preferably, the microcatheter 10 is further provided with a radiopaque marker 26, such as a band of platinum, palladium, gold or other material known in the art. The radiopaque marker can be provided in the form of a metal ring, which is positioned within the outer tubular jacket 42 prior to a heat shrinking step to secure the radiopaque marker within the outer tubular jacket.

Thus, the microcatheter of the present invention exhibits a series of zones of relatively increasing flexibility. The relative lengths of each zone can be varied to optimize the desired flexibility profile for particular intended applications of the catheter.

The first, most proximal zone contains the inner jacket 38. The spiral cut section 40 helps transition the change in flexibility from the first zone to the second zone.

The second zone extends from the distal end of inner jacket 38 to the distal end of spring 34. Distal segment 36 of spring 34, due to its open wound or "stretched" configuration provides a second flexibility transition between the second zone of the third zone.

The third zone extends from the distal end of spring 34 to the distal end tube 30. The spiral cut zone 32 on the tube 30 provides a third flexibility transition from the tube 30 to the fourth, most flexible zone.

The fourth zone is essentially no more than a floppy tip formed by the extension of outer jacket 42 beyond the distal end of tube 30.

In general, for intracranial applications, the second transition which is approximately at the distal end of spring 34 will be located at a point within the range of from about 70% to about 95% along the length of the catheter from the proximal end. The combination of the third and fourth zones make up the reminder of the catheter length.

The microcatheter 10 can be manufactured in accordance with a variety of techniques that will be known to those of skill in the art. Materials utilized in the construction of microcatheter 10 are preferably selected both for their physical properties in light of the intended end use of the microcatheter 10 as well as for their biocompatability in the intended use environment. Polymeric materials and metals which are sufficiently biocompatible to be used in intervascular procedures are well characterized in the prior art.

For example, polytetrafluoroethylene tubing, such as that suitable for tubular element 30, can be commercially obtained from Zeus, in Orangeburg, S.C. The distal section 32 can be provided with a spiral cut, such as by any of a variety of techniques that can be devised by those of skill in the art. In accordance with one technique, the PTFE or other tubing is placed onto a mandrel. The mandrel is attached to a machine with a predetermined screw thread. A cutting element such as a razor blade or other sharp instrument is placed across the tubing and the machine is activated to rotate the mandrel. As rotation of the machine (screw thread) occurs, the mandrel moves axially and rotationally causing the tubing to be cut in a spiral manner by the cutting implement. The machine can be set up to cut either a right or left hand spiral. The machine can also be set to cut continuous or variable pitch spirals, or multizone spiral sections in which each zone has a unique pitch. Spring coil 34 can be wrapped about a suitably sized mandrel as is known in the art, with the distal open wound section 36 formed by stretching.

The spring 34 is positioned concentrically around the tubular element 30, and the polyimide jacket 38 positioned concentrically about the spring coil 34. Polyimide tubing suitable for use as the polyimide jacket 38 can be obtained from MicroLumen Inc., Tampa, Fla. and spiral cut such as by the same technique discussed previously.

The subassembly is then positioned within an exterior jacket such as a polyethylene jacket having a recovered wall thickness of about 0.004 inches and an outside diameter of about 0.61 mm. The polyethylene jacket is thereafter exposed to a source of heat to shrink the jacket around the subassembly to provide a finished catheter body.

In use, a guide wire (not illustrated) is placed within the catheter 10 with its distal tip extending beyond the distal catheter tip. The assembled guide wire and catheter are then percutaneously inserted into the patient's vasculature and advanced to the appropriate treatment site. Appropriate positioning of the microcatheter 10 can be evaluated by visualizing the radiopaque marker 26.

Following proper positioning of the microcatheter 10, the guide wire is proximally withdrawn from the central lumen 22. Removal of the guidewire leaves the central lumen 22 available for whatever materials or instruments are necessary to carry out the desired procedure. For example, in one application of the present invention, drugs such as streptokinase may be introduced through central lumen 22 for delivery at the treatment site. Any of a variety of other medications, therapeutic or diagnostic tools, or the like may be advanced through central lumen 22 depending upon the intended application of the catheter.

Following treatment, the microcatheter 10 is proximally withdrawn from the patient's vasculature and the percutaneous puncture site is closed and dressed in accordance with conventional techniques.

Referring to FIG. 4, there is disclosed a further embodiment of the microcatheter of the present invention. The catheter 48 is configured to provide a continuous or essentially continuous variation in flexibility along its axial length. In this regard, the catheter has a relatively less flexible proximal end, and a highly flexible distal end, with no discrete zones or sudden changes in flexibility in between.

Microcatheter 48 has a proximal end 50, a distal end 52 and an elongate tubular flexible body 54, extending there between. Tubular body 54 comprises an elongate flexible tubular liner 56 extending from proximal end 50 to a distal terminus 62. The liner 56 in the illustrated embodiment has a solid wall from the proximal end 50 up to a transition point 58. In zone 60, which extends between transition point 58 and distal terminus 62, the liner 56 is provided with a spiral cut in accordance with techniques described previously herein. Depending upon the flexibility characteristics desired for a particular catheter, the axial length of the spiral cut zone 60 can be varied from about 0 (no spiral cut zone) to about 60 cm. Preferably, the length of spiral cut zone 60 will be within the range of from about 2 cm to about 20 cm, and, most preferably, the spiral cut zone 60 will be about 10 cm long.

The liner 56 in the illustrated embodiment is provided with a tapered wall thickness, from a relatively thick wall at the proximal end 50 to a relatively thin wall closer to the distal end 52. Preferably, the liner 56 has a substantially constant inside diameter throughout its axial length. In one embodiment of the invention, the liner 56 is provided with a wall thickness of about 0.012 at proximal end 50, and a wall thickness of about 0.001 in zone 60.

Preferably, the spiral cut zone 60 has an axial length within the range of from about 5 cm. to about 10 cm., with a variable or constant pitch spiral cut. The terminus 62 is preferably spaced apart from the distal end 52 of the catheter 48 by about 2 cm.

Liner 56 may be constructed from any of a variety of materials, depending upon the preferred construction techniques and desired physical properties of the microcatheter. In the preferred embodiment, the liner 56 comprises polytetrafluoroethylene (PTFE). Alternatively, other materials, such as TFE (softer than PTFE), other fluoropolymers, nylon, HDPE, and others that will be known to those of skill in the art can be adapted for use as the liner 56 of the present invention.

Continuously variable wall thickness tubing, such as that useful for liner 56, can be obtained by centerless grinding of constant wall PTFE tubing stock. Alternatively, liner 56 can be provided with a substantially constant wall thickness throughout, but with an increasing diameter in the proximal direction.

The variable wall thickness tubing can extend for essentially the entire length of the catheter such as from the proximal end up to the floppy tip. The variable wall thickness tubing can also be used in only one or more zones of a multizone catheter. For example, a two zone catheter may comprise a proximal section having a length of from about 50% to about 90% of the overall catheter length. The proximal section may have relatively constant flexibility throughout, such as the first or second zone in the embodiment of FIG. 3. The distal zone comprises a tapered segment as described above, preferably with an atraumatic flexible tip such as tip 52.

A coil 64, such as a spring, is disposed coaxially about the liner 56. Spring 64 extends from the proximal end 50 to approximately the terminus 62. In the illustrated embodiment, the radius of the spring is provided with a constant taper to correspond to the constant taper on the outside diameter of liner 56. In addition, the spring is preferably provided with a variable pitch such that the catheter 48 exhibits a continuous change in lateral flexibility from a relatively less flexible characteristic at its proximal end 50 to a relatively more flexible characteristic at its distal end 52.

Spring 64 can be constructed from any of a variety of materials, and be provided with any of a variety dimensions and other physical characteristics as will be appreciated by one of skill in the art in view of the disclosure herein. Preferably, spring 64 is provided with the physical characteristics and constructed from the materials identified previously herein.

An outer jacket 66 is disposed coaxially about the liner 56 and spring 64, and extends axially throughout the length of the microcatheter 48 from proximal end 50 to distal end 52. In one embodiment of the invention, the outer jacket 66 is about 150 cm. in length. A distal section 68 of the outer jacket 66 projects distally beyond the terminus 62. Distal section 68 preferably has a length within the range of from about 1 cm. to about 4 cm., and, more preferably, is about 2 cm. Distal section 68 may be provided with a radiopaque marker band (not illustrated) as has been discussed in connection with previous embodiments.

The catheter body 48 preferably has an overall length of about 150 cm., and diminishes radially in outside diameter from proximal end 50 to at least about terminus 62. Generally, the distal segment 68 will have a substantially constant diameter throughout its axial length. The outside diameter of the catheter 48 at proximal end 50 can be varied widely depending upon the intended application of the catheter. For cranial applications, the outside diameter will generally be less than about 0.065 inches, and, preferably, less than about 0.045 inches. The distal end 52 of the catheter 48 can also be varied in diameter depending upon the intended application of the catheter 48. For cranial applications, the distal end outside diameter will be less than about 0.038 inches and, preferably, is about 0.026 inches or smaller. The overall wall thickness of the catheter 48 can also be varied widely depending upon the desired physical properties of the catheter, and desired optimization of the central lumen extending therethrough. In the illustrated embodiment, as adapted for cranial applications, the wall thickness varies from about 0.012 inches at proximal end 50 to about 0.001 inches at distal end 52.

The catheter 48 may additionally be provided with any of a variety of adaptors, connectors, or manifolds as are well known in the art, and which may be secured to the proximal end 50 in accordance with known techniques. The use of the catheter 48 will be well understood to those of ordinary skill in the art, and, for example, may involve the same techniques disclosed in accordance with previous embodiments herein. All of the catheters disclosed herein may be used in accordance with the techniques disclosed in U.S. Pat. No. 4,739,768 to Engelson, the disclosure of which is incorporated herein by reference.

When any of the catheters of the present invention are embodied in the form of an angiographic catheter for diagnostic procedures, certain modifications may be desirable as will be apparent to those of ordinary skill in the art. In a diagnostic procedure, the primary purpose of these catheters is to allow injection of radiopaque contrast material into the bloodstream to permit imaging of the blood vessel in the form of an angiogram on X-ray film. During the process of diagnostic angiography, the contrast medium is usually injected at a rapid rate using a power injector. As a result, the contrast medium is forcefully discharged from the distal end hole of the catheter, creating a jet effect. This may produce an undesirable recoil of the catheter, and can also produce a dangerous complication such as subintimal injection of the contrast medium, in which the jet tunnels into the wall of the blood vessel.

To minimize the undesirable effect of recoil and the potential complication of subintimal injection, the catheter may be provided with a plurality of side holes (See, e.g. FIG. 5) to permit direct communication between the central lumen and the outside of the catheter laterally through the wall of the catheter. Effluent flow of contrast media (or medication in the case of a drug delivery catheter) through the side ports can be enhanced by minimizing or preventing flow through the distal opening of the catheter. Although the provision of a permanent cap or other occlusion at the distal end of the central lumen will increase effluent flow through the side ports, any such cap will also prevent the ability to advance single lumen catheters over a guidewire as is presently favored in the clinical setting.

Thus, any of the catheters of the present invention may additionally be provided with a valve at or near the distal end of the catheter, such as the valve described in U.S. Pat. No. 5,085,635 issued Feb. 4, 1992 to Cragg, the entirety of the disclosure of which is incorporated herein by reference.

Figure 5:
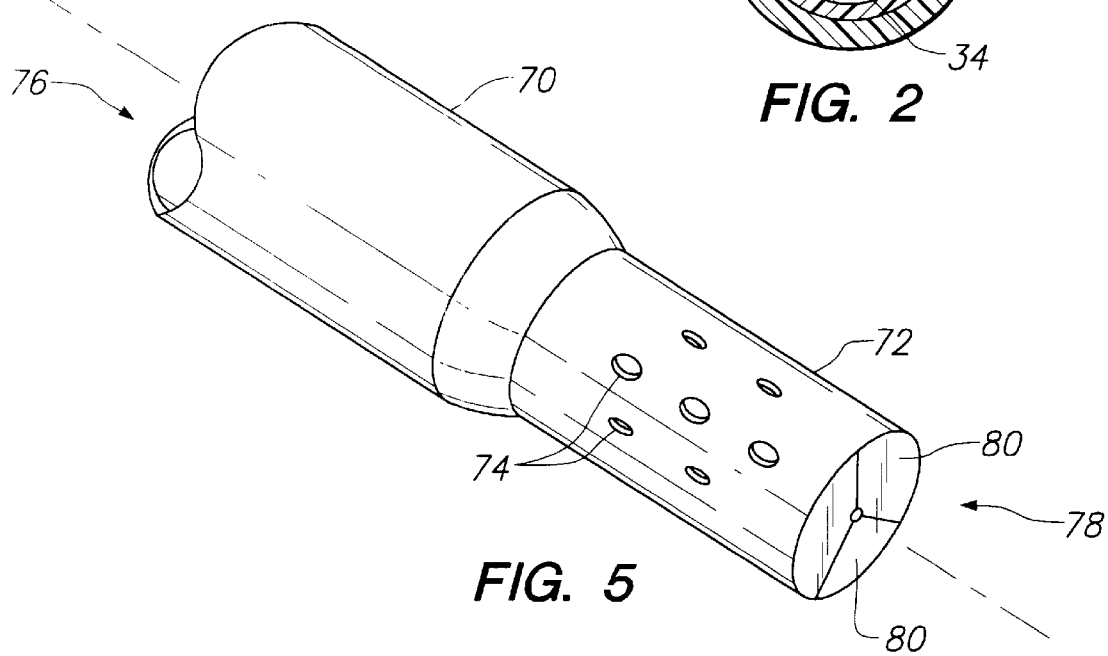
FIG. 5 is a fragmentary perspective view of the distal end of a catheter including a valve.

For example, referring to FIG. 5, there is illustrated a distal end fragment of an elongate tubular catheter 70 having a valve 78 thereon. Tubular catheter body 70, in the illustrated embodiment, is provided with a distal end segment 72 having a plurality of lateral apertures 74 thereon. Apertures 74 are placed in fluid communication with an external proximal fluid source (not illustrated) by way of axially extending central lumen 76.

Distal segment 72 is provided with a valve 78. In the illustrated embodiment, valve 78 comprises three coaptive leaflets 80. Leaflets 80 cooperate in a manner that will be well understood to those of skill in the art, to permit the passage of a guidewire (not illustrated) therethrough, and resiliently return to a relatively closed configuration as illustrated, following withdrawal of the guidewire. Leaflets 80 are preferably constructed from a relatively resilient material, to provide a bias to return to the closed configuration. Preferably, the bias provided by leaflets 80 will be sufficient to substantially resist the fluid pressure developed in central lumen 76 during infusion of contrast media or medication.

Depending upon the desired functionality of the catheter, valve 78 may be constructed to substantially prohibit fluid flow therethrough. Alternatively, valve 78 may be constructed to accommodate a relatively small fluid flow even in the "closed" position to prevent stagnation in the vessel at the distal end of the catheter as will be understood to those of skill in the art.

Leaflets 80 can be constructed in any of a variety of manners, such as by integral construction with the wall of distal segment 72, or by separate formation and subsequent attachment to the distal segment 72. For example, leaflets 80 may be separately molded or punched from sheet stock of a compatible material, such as a high density polyethylene, and thereafter adhered to the distal segment 72 such as by thermal bonding, solvent bonding, adhesives, welding, or any of a variety of other attachment techniques known in the art. Alternatively, the polymer chosen for use as a valve can be molded as a tube containing a closed septum. This molded unit can be heat fused or bonded onto the catheter tubing. The septum can then be cut to produce the valve leaflet described previously.

Figure 8:
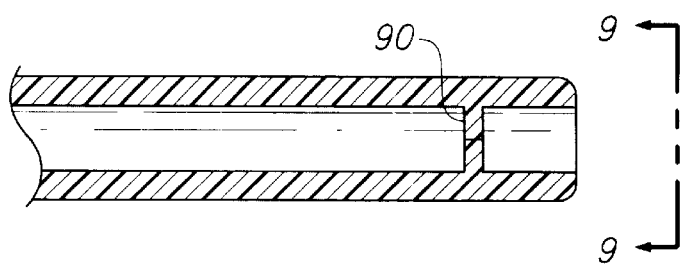
FIG. 8 is a side elevational cross-sectional view of a distal end of a catheter including an alternate embodiment of a valve.
Figure 9:
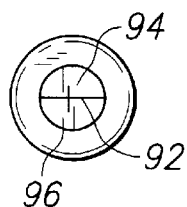
FIG. 9 is an end elevational view taken along the lines 9—9 of FIG. 8.

The number of leaflets can be varied as desired to accommodate catheter design and manufacturing issues. For example, a type of a two leaflet valve is illustrated in FIGS. 8 and 9. Four or more coaptive or cooperative leaflets can also be used.

A variety of alternate valve structures is disclosed in FIGS. 6–13. The selection and construction of a particular valve depends upon the desired characteristics of the finished catheter. For example, in some applications it may be desirable to inhibit any fluid flow through the distal valve, or to permit a relatively small volume fluid flow therethrough. Alternatively, it may be desirable to permit fluid flow in one direction and prevent or minimize fluid flow in the opposite direction. The desired direction of flow or inhibition of flow may be reversed depending upon whether the clinical objective is to infuse medication, or aspirate fluid from the lumen. Other uses will suggest themselves to those of skill in the art in view of the specific valve embodiments disclosed below.

Figure 6:
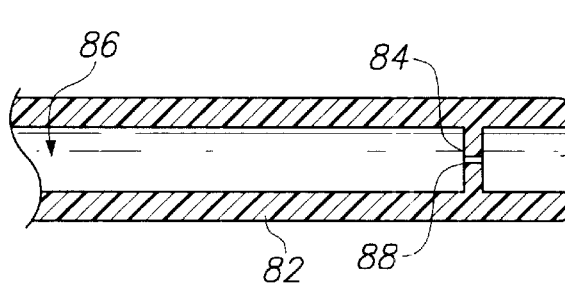
FIG. 6 is a side elevational cross sectional view of a distal end of a catheter including a valve.
Figure 7:
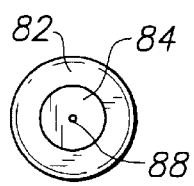
FIG. 7 is an end elevational view taken along the lines 7—7 in FIG. 6.

Referring to FIG. 6, there is illustrated a fragmentary view of a distal end 82 of a microcatheter in accordance with the present invention. A valve 84 is positioned within central lumen 86. Valve 84 comprises a membrane which may be formed integrally with or attached to the wall of catheter section 82. The membrane is provided with a central aperture 88 such as a 0.005 inch diameter opening, in a microcatheter having an outside diameter of about 0.026 inch. Aperture 88 permits the escape of pressurized media, such as contrast media or medication, sufficient to create a fluid flow in cavity 90, which may exist depending upon the construction of the catheter. In the absence of a sufficient flow through cavity 90, that cavity could provide the site for the formation of a thrombus and subsequent embolism with known detrimental sequela.

Aperture 88 may be sized to slidably receive a guidewire therethrough. Alternatively, aperture 88 may have a smaller cross-sectional dimension than the intended guidewire, but the valve 84 may be constructed from a material having sufficient resilience to permit an elastic expansion of the aperture 88 to accommodate the guidewire therethrough.

Referring to FIG. 8, there is disclosed an alternate embodiment of a valve 90. Valve 90 is constructed by providing a slit 92 through a valve membrane, to provide first and second valve leaflets 94 and 96. Construction of valve 90 from a relatively resilient material such as polyurethane, and having a wall thickness of about 0.005 in., will permit sufficient elasticity for the leaflets 94 and 96 to return to the core group position following removal of a guidewire therethrough. Valve 90 can also be constructed from any of a variety of elastomers, TPU, thermoplastic rubber, or thermoset rubber.

Figures 10, 11:
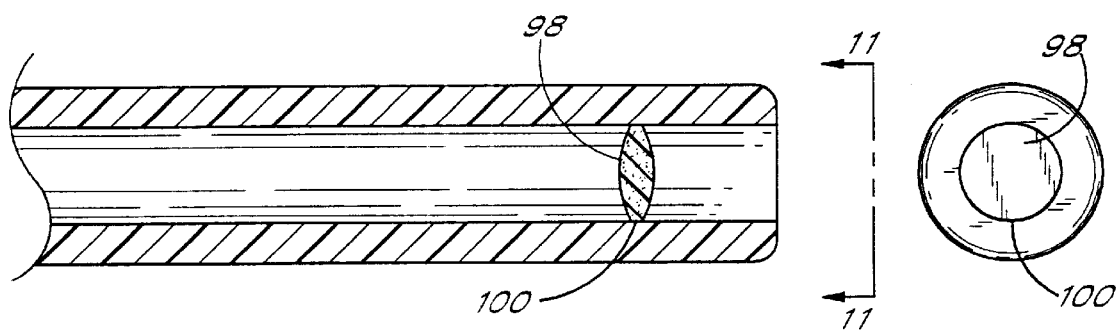
FIG. 10 is a side elevational cross-sectional view of an alternate embodiment of a valve.
FIG. 11 is an end elevational view taken along the lines 11—11 in FIG. 10.

Referring to FIG. 10, there is disclosed a valve 98 formed from a self-healing membrane or plug positioned within the central lumen. In one embodiment, valve 98 comprises a silicone gel plug attached at least one point 100 to the wall of the catheter. The silicone gel plug may be hinged about attachment point 100 within the central lumen by sufficient force, such as by a guidewire, and yet will return to occlude the central lumen upon removal of the guidewire. The silicone gel plug may be provided with an annular valve seat on the interior surface of the catheter body, as will be appreciated by those of skill in the art. Depending upon the desired direction of resistance to flow, the valve seat can be positioned on either the proximal or distal side of the gel plug.

Figures 12, 13:
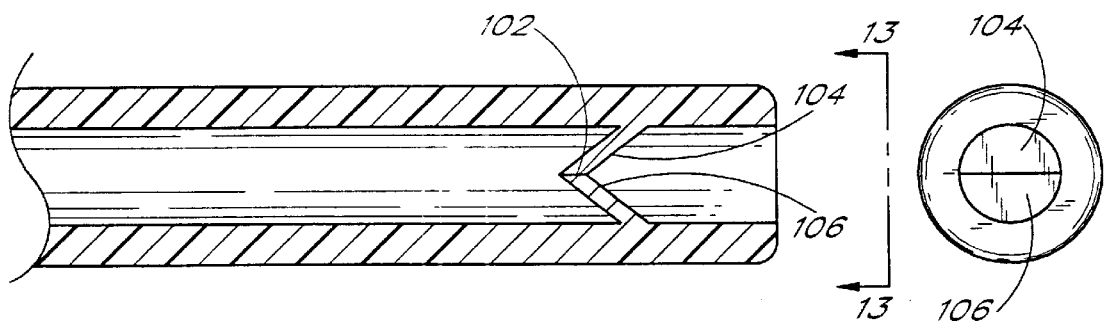
FIG. 12 is a side elevational cross-sectional view of an alternate embodiment of a valve.
FIG. 13 is an end elevational view taken along the lines 13—13 in FIG. 12.

A further embodiment of a valve in accordance with the present invention is illustrated in FIG. 12. Valve 102 is in the configuration of a generally conical or tapered duckbill valve. Duckbill valve 102 comprises at least a first and second leaflet 104 and 106, inclining radially inwardly in the proximal direction in the illustrated embodiment. Leaflets 104 and 106 as illustrated permit advancement of the catheter over a guidewire in the distal direction, and, following proximal withdrawal of the guidewire, will resist the escape of pressurized fluid out of the distal end of the catheter. In addition, duckbill valve 102 will permit the aspiration of fluid, if desired, from the vessel into the catheter.

Referring to FIG. 14, there is illustrated an embodiment of the microcatheter of the present invention having a distal inflatable balloon thereon. The illustrated balloon catheter embodiment of the present invention also incorporates a distal valve in the central lumen as discussed previously. The combination of the valve with an inflatable balloon in the microcatheter of the present invention permits a particularly small diameter catheter in view of the ability of the catheter to utilize a single central lumen for both placement of the catheter over a guidewire, and also as an inflation lumen for inflating the balloon.

The balloon catheter 108 generally comprises an elongate flexible tubular body 110, which can be manufactured in accordance with any of a variety of conventional single lumen catheter body techniques. For example, body 110 can be formed by extrusion from high density polyethylene or any of a variety of other well known catheter body materials. Preferably, the tubular body 110 is constructed in accordance with one of the embodiments of the invention previously described herein. For the purpose of FIG. 14, only the distal, balloon end of the catheter will be illustrated.

The distal end of catheter 110 is provided with an inflatable balloon 112. Balloon 112 is connected to the catheter body 110 at a proximal seal 114 and a distal seal 116 as is known in the art, thereby creating an enclosed interior space 118. Interior space 118 is placed in fluid communication with a proximal source of inflation media (not illustrated) by way of an elongate central lumen 120 which extends axially throughout the length of the catheter. Central lumen 120 is in fluid communication with the interior 118 of balloon 112 by one or more inflation side holes 122.

The construction material, axial length, as well as inflated diameter of the balloon 112, can be varied widely depending upon the intended clinical use, as is well understood in the art. In one preferred embodiment of the invention, the balloon 112 comprises polyolefin elastomer such as Dow, Engage SM8400, and is constructed to have an inflated profile with a diameter of about 4 mm at 0.5 ATM and an axial working length of about 1 cm. Other lengths and diameters, as well as other balloon characteristics can be readily incorporated into the microcatheter of the present invention, as may be desired for a particular intended application.

The distal end 124 of tubular body 110 is provided with a valve 126. Valve 126 may be constructed in accordance with any of the embodiments discussed previously herein. In one particular embodiment of the invention, valve 126 comprises a three leaflet construction, as has been discussed.

The valve 126 permits the catheter to be advanced over a guidewire such as during the positioning step as has been discussed. Following positioning of the balloon at the desired treatment site, the guidewire may be proximally withdrawn from central lumen 120. Valve 126 closes due to its inherent resilient properties. Thereafter, inflation media may be introduced into the central lumen 120. Inflation media is inhibited from exiting the distal end of central lumen 120 by closed valve 126. Instead, the inflation media escapes central lumen 120 through side port 122, to inflate the interior 118 of balloon 112.

In the embodiment of the invention described below, the valve 126 inhibits or substantially inhibits escape of inflation media up to an inflation pressure of about 7 atmospheres. Resistance to excessive leakage at higher inflation pressures can be achieved through modifications of the valve design, as will be readily apparent to those of skill in the art in view of the disclosure herein. For example, increasing the thickness of the valve leaflets, or using a less flexible material for the valve leaflets will increase the break pressure of the valve 126. In addition, structural modifications can be made to the design of the valve 126 which will increase its break pressure.

In the embodiment illustrated in FIG. 14, a distal valve assembly 128 may be constructed separately from the tubular body 110, and secured thereto as a subsequent assembly step. Valve assembly 128 can be constructed in any of a variety of ways, such as by molding as an integral unit. In one embodiment, the valve assembly 128 can be injection molded from polyolefin or polyurethane elastomers as a tubular subassembly having an axial length of about 0.20 inches an inside diameter of about 0.018 inches and an outside diameter of about 0.038 inches. The central lumen is blocked by a continuous diaphragm having a thickness of about 0.008 inches. The diaphragm can be provided with three slits as a post molding step to produce a three leaflet valve 126.

The valve assembly 128 may thereafter be secured to the distal end of tubular body 110, such as by heat fusing or bonding. As a further reinforcement step, the distal seal 116 on balloon 112 preferably extends axially a sufficient distance to overlap the junction between the distal end of tubular body 110 and the proximal end of valve assembly 128.

In accordance with a method of the present invention, an intravascular site is identified in a soft tissue such as the brain which requires dilatation to improve blood flow. A balloon microcatheter 108 in accordance with the present invention is percutaneously introduced into the patient's vascular system and transluminally advanced to the treatment site. Preferably, the advancing and positioning steps of the method are accomplished through the use of an elongate flexible guidewire extending axially throughout the length of the central lumen 120, as is well understood in the art.

Following positioning of the balloon 112 at the treatment site, the guidewire is proximally withdrawn from the catheter. As the distal end of the guidewire advances proximally through valve 126, the valve leaflets move into a closed position as has been discussed. Thereafter, inflation media is introduced into central lumen 120 at the desired pressure to inflate balloon 112. During inflation, the valve 126 prevents or substantially prevents the escape of inflation media out the distal end of the catheter 108, thereby permitting dilatation of the balloon 112. Depending upon valve design, a small amount of inflation media may escape through the valve 126, if desired, to minimize the occurrence of stagnant blood in the distal tip of the balloon microcatheter 108.

Following dilatation of balloon 112, inflation media is withdrawn from the balloon 112 by way of central lumen 120 as is known in the art to collapse the balloon 112. The balloon microcatheter 108 may then be proximally withdrawn from the patient, and the patient is treated in accordance with conventional post dilatation protocols.

Although the present invention has been described in terms of certain preferred embodiments, other embodiments will become apparent to those of ordinary skill in the art following a review of the disclosure herein. Additional embodiments that are apparent to those of skill in the art in view of this disclosure are intended to be within the scope of the present invention, and the foregoing disclosure is, thus, intended not by limitation, but merely to illustrate a specific application of the invention. The scope of the invention is intended to be defined by the scope of the appended claims.

What is claimed is:

1. A catheter, comprising:
    an elongate flexible tubular body having proximal and distal ends, and at least one central lumen extending axially therethrough; and
    a spiral cut tubular member within the tubular body, the spiral cut tubular member having at least one flexibility gradient zone, said flexibility gradient zone having a first flexibility at a proximal end thereof, a second flexibility at a distal end thereof, and a continuous change in flexibility along the length of the zone from the first flexibility to the second flexibility.

2. A catheter as in claim 1, wherein said flexibility zone extends for at least about 98% of the length of the catheter.

3. A catheter as in claim 1, wherein said flexibility zone extends for at least about 75% of the length of the catheter.

4. A catheter as in claim 1, wherein said tubular body has a wall thickness between an outside surface of the tubular body and the lumen extending therethrough, and the wall thickness at the proximal end of the flexibility zone is greater than the wall thickness at the distal end of the flexibility zone.

5. A catheter as in claim 1, wherein said flexibility zone comprises a continuous change in wall thickness from the proximal end to the distal end thereof.

6. A catheter as in claim 1, wherein said flexibility zone extends for at least about 148 cm, and has a wall thickness within the range of from about 0.009 inches to about 0.012 inches at the proximal end thereof and within the range of from about 0.0005 inches to about 0.002 inches at the distal end thereof.

7. A catheter as in claim 1, wherein said flexibility zone extends for at least about 148 cm, and has a wall thickness of about 0.012 inches at the proximal end thereof and about 0.001 inches at the distal end thereof.

8. A catheter, comprising:
    an elongate flexible tubular body having proximal and distal ends, and at least one central lumen extending axially therethrough; and
    a spiral cut tubular member within the tubular body, wherein the spiral cut tubular member has a first flexibility at a proximal end thereof, a second flexibility at a distal end thereof, and a continuous change in flexibility along the length of the spiral cut tubular member from the first flexibility to the second flexibility.

9. A catheter as in claim 8, wherein said spiral cut tubular member extends for at least about 75% of the length of the catheter.

10. A catheter as in claim 8, wherein said spiral cut tubular member has a wall thickness between an outside surface of the tubular member and a lumen extending therethrough, and the wall thickness at the proximal end of the spiral cut tubular member is greater than the wall thickness at the distal end of the spiral cut tubular member.

11. A catheter as in claim 8, wherein said spiral cut tubular member comprises a continuous change in wall thickness from the proximal end to the distal end thereof.

12. A catheter as in claim 11, wherein said spiral cut tubular member has a lumen with a constant diameter between the proximal and distal ends of the tubular member.

13. A catheter as in claim 8, wherein said spiral cut tubular member extends for at least about 148 cm, and has a wall thickness of about 0.012 inches at the proximal end thereof and about 0.001 inches at the distal end thereof.

* * * * *